Figure 1:
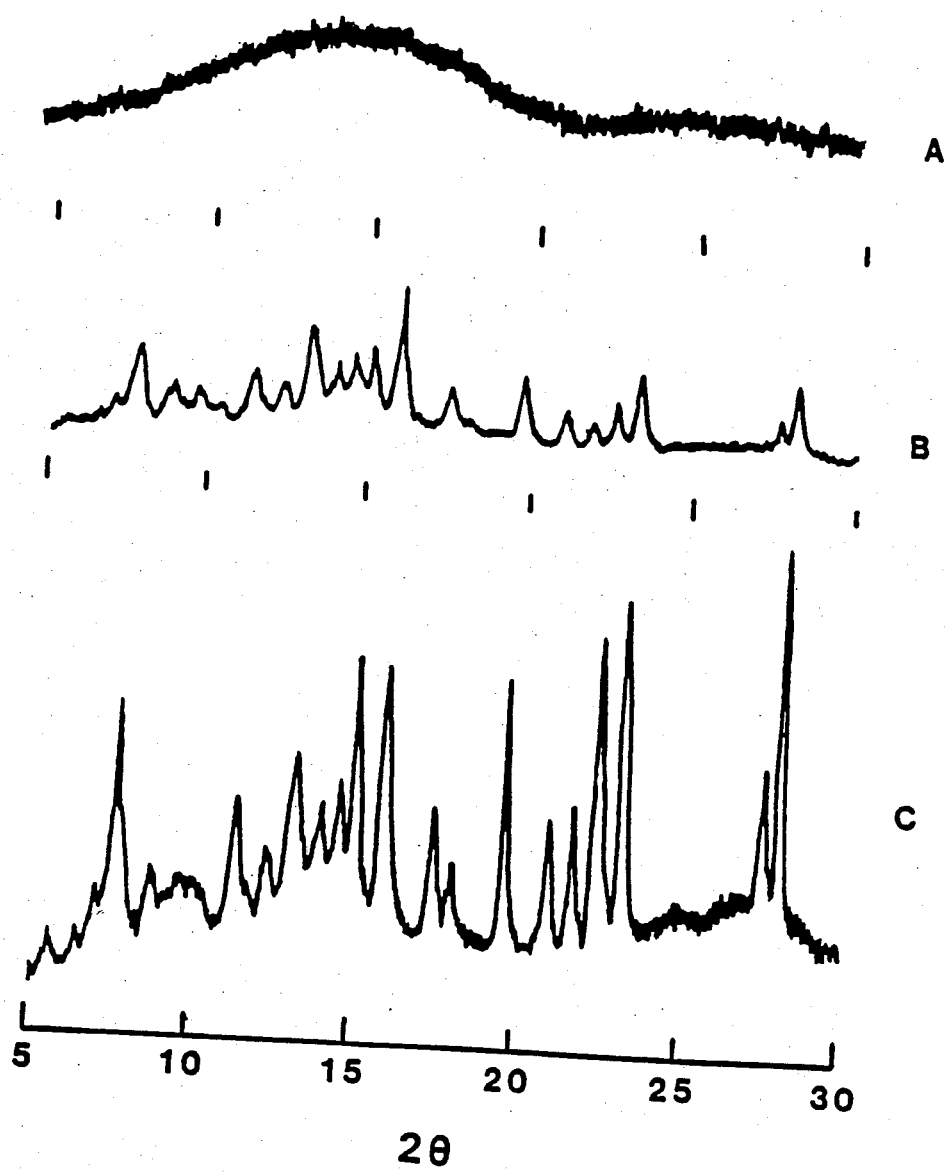

United States Patent [19]
Chan et al.

[11] Patent Number: 4,629,782
[45] Date of Patent: Dec. 16, 1986

[54] CRYSTALLINE FORM OF N-ACETYLMURAMYL-L-α-AMINOBUTYRYL-D-ISOGLUTAMINE

[75] Inventors: Tai W. Chan, Palo Alto; Allyn R. Becker, Half Moon Bay, both of Calif.

[73] Assignee: Syntex (U.S.A.) Inc., Palo Alto, Calif.

[21] Appl. No.: 684,753

[22] Filed: Dec. 21, 1984

[51] Int. Cl.[4] ............................................. C07K 9/00
[52] U.S. Cl. ................................................... 530/322
[58] Field of Search ....................................... 530/322

[56] References Cited

U.S. PATENT DOCUMENTS 4,082,736  4/1978  Jones et al. ................... 260/112.5 R Primary Examiner—Delbert R. Phillips
Attorney, Agent, or Firm—Grant D. Green; Tom M. Moran; Alan M. Krubiner

[57] ABSTRACT

Crystalline N-acetylmuramyl-L-α-aminobutyryl-D-isoglutamine monohydrate useful as an adjuvant for vaccines and as an immunostimulant.

2 Claims, 1 Drawing Figure

CRYSTALLINE FORM OF N-ACETYLMURAMYL-L-α-AMINOBUTYRYL-D-ISOGLUTAMINE

BACKGROUND OF THE INVENTION

N-[2-acetamido-3-O-(D-ethyl-1-carbonyl)-2-deoxy-D-glucose]-L-alanyl-D-isoglutamine (muramyldipeptide or MDP) was proposed in 1974–1975 (Ellouz, et al., Biochem, Biophys. Res. Comm., 59, 317 (1974) and Merser, et al., Biochem. Biophys. Res. Comm., 66, 1316 (1975) to be the minimal structure required to express the full spectrum of adjuvant activity when substituted for mycobacteria in Freund's complete adjuvant. Since that time, considerable synthetic efforts, coupled with bioassays have resulted in chemical modifications of MDP with improved immunoadjuvant properties and reduced toxicity.

For example, U.S. Pat. No. 4,082,736, issued Apr. 4, 1978 to Jones, Moffatt and Nestor, describes a family of compounds which are useful as immunological adjuvants. One of the compounds encompassed within the scope of that patent is N-acetylmuramyl-L-α-aminobutyryl-D-isoglutamine. This compound is particularly useful as an adjuvant for vaccines, but previously was known only in its amorphous form. In this form, the compound suffered disadvantages of being hygroscopic and chemically reactive at high temperatures. These disadvantages presented certain handling, storage and formulation problems.

It has now been found that the compound N-acetylmuramyl-L-α-aminobutyryl-D-isoglutamine (ABU-MDP) can be prepared as a crystalline monohydrate. This novel crystalline monohydrate is substantially more stable under heat and humidity than is amorphous ABU-MDP and thus overcomes the previous disadvantages of the amorphous ABU-MDP. The new crystalline monohydrate is useful as an adjuvant for vaccines and as an immunostimulant.

SUMMARY OF THE INVENTION

This invention relates to stable, crystalline acetylmuramyl-L-α-aminobutyryl-D-isoglutamine monohydrate, the compound of formula 1

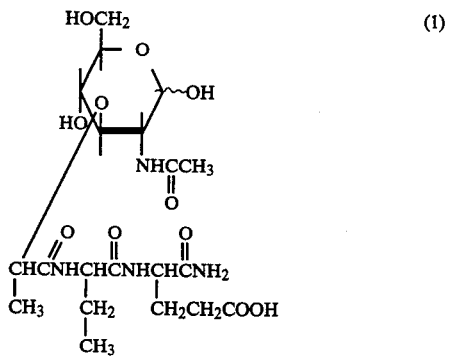

This crystalline monohydrate consists of a mixture of about 75–86% of the α anomer, the remainder being the β-anomer.

This invention also relates to a process for preparing crystalline N-acetylmuramyl-L-α-aminobutyryl-D-isoglutamine monohydrate.

Further Description of the Invention

The crystalline monohydrate of formula (1) has about one mole of water associated with a mole of ABU-MDP in the crystalline structure. Thus the crystalline monohydrate will be about 3.4% by weight of water, although this percentage may be as high as about 5.6% due to surface-bound or occluded water. The compound of formula (1) is a mixture of about 75–86% (preferably about 78–82%) by weight of the α-anomer and about 25–14% (preferably about 22–18%) by weight of the β-anomer. These varying percentages of α- and β-anomers may contribute to the variance of the percentage of water in the compound of this invention.

The compound of this invention is best characterized by determining the X-ray powder diffraction pattern in accordance with procedures which are known in the art. For a discussion of these techniques see J. Haleblian, J. Pharm. Sci. 64, 1269–1288, 1975 and J. Haleblian W. McCrone, J. Pharm. Sci., 58, 911–929, 1969, which is incorporated herein by reference. Although the X-ray powder diffraction patterns of the compound of formula (1) made by different routes may vary slightly in intensity, the peaks are at the same 2 θ values and thus represent the same crystalline structure. For example, FIGS. 1B and 1C each show the X-ray pattern for the compound of formula (1) prepared by two different routes.

Physically, the crystalline monohydrate of this invention is obtained as crystals which are aggregates of birefringent, rod-like particles or needles. In the aggregate, these crystals appear as a white powder which is much less hygroscopic than the amorphous ABU-MDP previously known.

The compound of this invention is prepared by contacting amorphous ABU-MDP with water for a sufficient time to form the crystalline monohydrate of formula (1). The contact is made with water in its liquid and/or gaseous state at temperatures of 0° C. to about 75° C., preferably at about 10° to 50° C. and most preferably at ambient temperatures (i.e. about 20°–25° C.). If liquid water is used, the amorphous ABU-MDP is first dissolved in the water then allowed to crystallize out. Crystallization is achieved by removing water (e.g. by heat or evaporation) from the solution to about the point of saturation, until crystallization takes place, by cooling the solution to the point of crystallization, or simply by adding the amorphous ABU-MDP to water until the saturation point is reached while maintaining the solution at ambient temperature until crystallization occurs. The resulting crystals are then separated from the mother liquor by usual means such as filtration, centrifugation and the like and dried at ambient temperatures (about 20°–25° C.), at atmospheric pressure or less to give the desired crystalline, monohydrate of formula (1).

If gaseous water is used, the contact is made simply by contacting amorphous ABU-MDP with air of relative humidity of about 40–100%, preferably about 60–80%, for about two hours to several days, depending on the amount of amorphous ABU-MDP and the surface area available for contact. Generally this is easily done by placing amorphous ABU-MDP in a chamber having high humidity (e.g. 70% or more) for two hours or more (until the ABU-MDP turns into a viscuous liquid and crystallizes out as the crystalline monohydrate).

Preparation A

Amorphous ABU MDP is prepared in accordance with the process set forth in the appropriate examples of U.S. Pat. No. 4,082,736 to give a lyophilized powder consisting of irregular isotropic, glass-like plates. This material was then used in the following examples.

A further understanding of the invention can be had from the following non-limiting Examples.

EXAMPLE I

A. The compound of formula (1) was prepared by adding 504 mg of amorphous ABU MDP to 0.5 ml of water in a test tube. The test tube was securely capped and placed in a water bath at 25° C. and tumbled for about 4 days, during which time the solution slowly turned into a white paste. The paste was filtered, air dried and ground to a fine white powder of the crystalline monohydrate of formula (1).

B. By following the above procedure, the same results are achieved using 307 mg of amorphous ABU-MDP and 0.4 ml of an aqueous 0.9% NaCl solution or 650 mg of amorphous ABU-MDP in 0.624 ml of an aqueous solution of NaOH (final pH 3.96).

C. Similar results are achieved by fully dissolving 500 mg of amorphous ABU-MDP in 0.624 ml of aqueous NaOH (final pH 4.06) and tumbling for about one day.

D. 412.5 Mg of amorphous ABU-MDP were added to 0.2 ml of water in a test tube. After 10 minutes a white paste was formed, which, after filtration was determined to be the crystalline monohydrate of formula (1).

EXAMPLE II

A. The compound of formula (1) was also prepared by placing 200 mg of amorphous ABU-MDP powder in an open cylindrical vial in a 160 mm desiccator containing a beaker of about 50 ml of a saturated solution of sodium acetate. The amorphous ABU-MDP was maintained in the desiccator for five days at 25° C. and gradually was converted to a viscous solution and then a white, solid mass. This material was then ground to a fine white power of crystalline monohydrate of formula (1).

B. The weight gain due to the absorption of moisture by amorphous ABU-MDP was followed by using a Perkin-Elmer TGS-2 thermogravimetric balance over a period of 25 hours. Exposure of anhydrous ABU-MDP to 76% relative humidity resulted in an initial sharp gain in weight, followed by a slow decrease in weight after reaching a maximum. The resulting material was shown to be identical to the crystalline monohydrate prepared by the methods described in Examples I A-D. Amorphous ABU-MDP was converted to the crystalline form by the following pathway:

EXAMPLE III

X-ray powder diffraction patterns of samples of the material obtained from Preparation A (amorphous ABU-MDP), Example I and Example II were determined on a General Electric X-ray diffractometer with Ni-filtered CuK$_\alpha$ radiation. The scanning angle was from 5° to 30° 2 $\theta$, at 2° per minute. FIG. 1 shows the X-ray diffraction patterns of (A) amorphous ABU-MDP, (B) the crystalline monohydrate obtained in accordance with Example I, and (C) the crystalline monohydrate obtained in accordance with Example II.

EXAMPLE IV

This example describes a method for distinguishing amorphous ABU-MDP from the crystalline monohydrate of formula (1) using differential scanning calorimetry (DSC). The instrument used was a Perkin-Elmer DSC-2. The heating rate was 10° C. per minute, and the sensitivity range was 5 mcal per second.

The DSC thermogram for amorphous ABU-MDP showed only a broad endotherm at 45°-129° C. and no further endotherm(s).

On the other hand, the DSC thermogram for the crystalline monohydrate of formula (1) showed two endothermic transitions, one at 80°-130° C. and the other at 175° C. The first endotherm was due to the release of water and the second seemed to be due to the melting of the anhydrous material formed by the loss of water during the first endotherm. If the material remaining after the 80°-130° C. endotherm is then heated to 140° C., cooled to 40° C. under anhydrous conditions, and reheated to 140° C. again, the thermogram obtained on the resulting material did not show the initial endothermic transition, as the water of crystallization had already been removed. However, on exposure to air (relative humidity approximately 40%) for 2 or 3 hours, the first endothermic transition was restored, indicating that the anhydrous solid had regained its water of hydration.

EXAMPLE V

The crystalline monohydrate of formula (1) is further characterized by thermal microscopy using a Leitz polarized light microscope in conjunction with a Mettler FP52 hot stage equipped with a Mettler FP5 central unit. Using this technique, the crystalline monohydrate prepared according to Examples I and II was found to release water as bubbles at about 150° C. and began decomposing at about 159° C.

EXAMPLE VI

The mole ratio of water to ABU-MDP in the crystalline monohydrate of formula (1) was determined by thermogravimetric analysis (TGA). A small amount of the monohydrate prepared in accordance with Example II was dried under "house" vacuum for 12 hours and then exposed to air for about 3 hours. TGA of the resulting crystals showed that the release of water on heating proceeded in two stages: an initial weight loss of 1.5% followed by a further weight loss of 4.09%. These results indicate that the crystalline monohydrate is slightly hygroscopic; the 1.5% weight loss probably being due to water absorbed on the surface which is not part of the crystal structure. This analysis was conducted with a Perkin Elmer TGS-2 thermogravimetric balance. The heating rate was 2.5° C. per minute from 40° C. to 160° C. A dry nitrogen purge was maintained throughout each run.

EXAMPLE VII

The stability of amorphous ABU-MDP and the crystalline monohydrate of formula (1) was determined by HPLC analysis. The HPLC system consisted of a Spectra Physics model 3500 Pump operated at 1.0 ml/min, a Schoeffel variable wavelength detector monitoring at 210 nm, and an Altex Ultrasphere 5 micron octadecyl silane column (25 cm×4.6 mm). The mobile phase was 9% methanol—91% 0.1M potassium dihydrogen phosphate buffer adjusted to a pH of 3.0 with concentrated phosphoric acid. The percentages given in Table 1 are the percent of starting compound determined to be remaining after storage of a sample of each for 4 days at 80° C. and 76% relative humidity. Breakdown products were not isolated or characterized.

TABLE 1

| Material | % Remaining |
|---|---|
| Amorphous ABU-MDP | 5% |
| Crystalline monohydrate | 83% |

EXAMPLE VIII

This example explains how to determine the ratio of the $\alpha$-anomer to the $\beta$-anomer in the crystalline monohydrate of formula (1). The mutarotation between the two anomers can be described as follows:

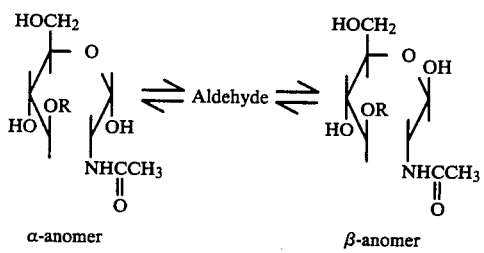

α-anomer    β-anomer

R is the propionyl-L-$\alpha$-aminobutyryl-D-isoglutamine moiety.

Upon dissolving the crystalline monohydrate in water and repeatedly analyzing the anomer ratio by HPLC, the first eluting peak, the $\beta$-anomer, was found to grow in area at the expense of the second eluting peak. This demonstrates that the amoner ratio in the solid state is different from that in solution at equilibrium. The $\alpha/\beta$ ratio of the area of the two peaks obtained by extrapolation to zero time was 4.02 to 1. The $\alpha/\beta$ ratio in solution at equilibrium was 2 to 1. These results indicate that the percentage of the $\alpha$-anomer in the crystalline monohydrate of formula (1) is higher than that in solution. Although the crystalline monohydrate was enriched in the $\alpha$-anomer relative to that observed in solution, it was not possible to obtain a monohydrate form of Compound I which contained only one of the two anomers. This confirms the presence of two anomeric forms in the crystalline monohydrate.

EXAMPLE IX

The crystalline monohydrate of this invention is less hygroscopic than amorphous ABU-MDP. This is readily observed by visually comparing samples of each in separate containers at 76% relative humidity and ambient temperature. Under these conditions the amorphous ABU-MDP turns into a syrupy solution within about an hour while the crystalline monohydrate remains a solid.

What is claimed is:
1. Crystalline N-acetylmuramyl-L-$\alpha$-aminobutyryl-D-isoglutamine monohydrate.
2. A method for making crystalline N-acetylmuramyl-L-$\alpha$-aminobutyryl-D-isoglutamine monohydrate which method comprises contacting amorphous N-acetylmuramyl-L-$\alpha$-aminobutyrl-D-isoglutamine with water for a time sufficient to form the desired crystalline monohydrate.

* * * * *